(12) United States Patent
Fadell et al.

(10) Patent No.: US 10,836,990 B2
(45) Date of Patent: Nov. 17, 2020

(54) SENSOR INTERFACE FOR SINGLE-USE CONTAINERS

(71) Applicant: Rosemount Inc., Shakopee, MN (US)

(72) Inventors: Paul R. Fadell, Cypress, MN (US); Joshua M. Price, Brenham, TX (US)

(73) Assignee: CyberOptics Corporation, Golden Valley, MN (US)

( * ) Notice: Subject to any disclaimer, the term of this patent is extended or adjusted under 35 U.S.C. 154(b) by 0 days.

(21) Appl. No.: 15/390,154

(22) Filed: Dec. 23, 2016

(65) Prior Publication Data

US 2018/0179486 A1 Jun. 28, 2018

(51) Int. Cl.
*G01N 1/00* (2006.01)
*C12M 1/34* (2006.01)
(Continued)

(52) U.S. Cl.
CPC .......... *C12M 41/40* (2013.01); *C12M 23/28* (2013.01); *C12M 23/46* (2013.01)

(58) Field of Classification Search
CPC ...................................................... C12M 41/40
See application file for complete search history.

(56) References Cited

U.S. PATENT DOCUMENTS 1,786,101 A * 12/1930 Welch ................. B60B 9/20
152/10
3,374,674 A 3/1968 Schwartzman
(Continued)

FOREIGN PATENT DOCUMENTS

CN 101839776 A 9/2010
CN 205620076 U 10/2016
(Continued)

OTHER PUBLICATIONS

International Search Report and Written Opinion for PCT/US2016024859, dated Jul. 12, 2016, 11 pages.
(Continued)

*Primary Examiner* — Jyoti Nagpaul
(74) *Attorney, Agent, or Firm* — Christopher R. Christenson; Kelly, Holt & Christenson PLLC

(57) ABSTRACT

A single-use sensor interface for coupling a single-use container to a re-usable sensing instrument is provided. The single-use sensor interface includes a polymeric flange couplable to a wall of the single-use container. The polymeric flange has a sidewall and an interface portion configured to receive a deflectable polymeric diaphragm. A deflectable polymeric diaphragm is coupled to the interface portion of the polymeric flange. An instrument coupling portion is sealingly coupled to the polymeric flange. The instrument coupling portion is configured to couple to the re-usable sensing instrument. Another single-use sensor interface for coupling a single-use container to a re-usable sensing instrument includes a polymeric hose adapter and at least one instrument attachment portion. The polymeric hose adapter portion has at least one hose barb configured to retain a hose slid thereover. The hose adapter portion has at least one interface portion that is configured to receive a deflectable polymeric diaphragm. A deflectable polymeric diaphragm is coupled to the interface portion. At least one instrument attachment portion is coupled to the hose adapter portion. The at least one instrument attachment portion has a cylindrical sidewall.

13 Claims, 11 Drawing Sheets

(51) Int. Cl.
*C12M 1/00* (2006.01)
*C12M 3/00* (2006.01)

(56) References Cited

U.S. PATENT DOCUMENTS

| | | | |
|---|---|---|---|
| 3,821,897 | A | 7/1974 | Frazel |
| 4,297,871 | A | 11/1981 | Wright |
| 4,989,456 | A | 2/1991 | Slupecky |
| 5,460,049 | A | 10/1995 | Kirsch |
| 6,602,401 | B1 | 8/2003 | Feng |
| 6,894,502 | B2 | 5/2005 | Feng et al. |
| 6,979,307 | B2 | 12/2005 | Beretta |
| 7,784,353 | B1 * | 8/2010 | Feldmeier ............ G01L 19/0023 73/744 |
| 7,924,017 | B2 | 4/2011 | Ammann et al. |
| 7,972,495 | B1 | 7/2011 | Millar et al. |
| 8,123,397 | B2 | 2/2012 | Baumfalk et al. |
| 8,252,582 | B2 | 8/2012 | Bamfalk et al. |
| 8,304,231 | B2 | 11/2012 | Roll |
| 8,640,560 | B2 | 2/2014 | Burke |
| 8,900,855 | B2 | 2/2014 | Feng et al. |
| 8,828,202 | B2 | 9/2014 | Feng |
| 9,029,130 | B2 | 5/2015 | Feng et al. |
| 9,267,100 | B2 | 2/2016 | Selker et al. |
| 2001/0028865 | A1 | 10/2001 | Cummings et al. |
| 2002/0072084 | A1 | 6/2002 | Meserol et al. |
| 2003/0168403 | A1 | 9/2003 | Corcho-Sanchez |
| 2004/0027912 | A1 | 2/2004 | Bibbo et al. |
| 2004/0140211 | A1 | 7/2004 | Broy et al. |
| 2005/0163667 | A1 | 7/2005 | Krause |
| 2005/0225035 | A1 | 10/2005 | Sundet |
| 2006/0228804 | A1 | 10/2006 | Xu et al. |
| 2007/0151349 | A1 | 7/2007 | Schumacher et al. |
| 2008/0032389 | A1 | 2/2008 | Selker et al. |
| 2008/0053255 | A1 | 3/2008 | Furey et al. |
| 2009/0130704 | A1 | 5/2009 | Gyure |
| 2009/0139298 | A1 | 6/2009 | Klees et al. |
| 2010/0302008 | A1 | 12/2010 | Engelstad et al. |
| 2011/0041619 | A1 | 2/2011 | Delbos et al. |
| 2011/0201100 | A1 | 8/2011 | Proulx |
| 2012/0240666 | A1 | 9/2012 | Blomberg et al. |
| 2012/0242993 | A1 | 9/2012 | Shick et al. |
| 2012/0290268 | A1 | 11/2012 | Bey |
| 2013/0055821 | A1 | 3/2013 | Bentley |
| 2013/0145818 | A1 | 6/2013 | Allgauer et al. |
| 2014/0207016 | A1 | 7/2014 | Addington |
| 2015/0030514 | A1 | 1/2015 | Feltham |
| 2015/0316528 | A1 | 11/2015 | Schumacher |
| 2016/0298068 | A1 | 10/2016 | Schumacher |
| 2017/0003183 | A1 | 1/2017 | Fadell et al. |

FOREIGN PATENT DOCUMENTS

| | | |
|---|---|---|
| EP | 0399227 B1 | 11/1990 |
| EP | 0753737 B1 | 1/1997 |
| EP | 2065701 A3 | 3/2009 |
| GB | 2364125 | 1/2001 |
| JP | 2008039523 | 2/2008 |
| WO | 1992-001218 | 1/1992 |
| WO | 2008016411 A1 | 2/2008 |
| WO | 2009-017765 | 2/2009 |
| WO | 2013-162394 A1 | 10/2013 |
| WO | 2013180853 A1 | 12/2013 |

OTHER PUBLICATIONS

International Search Report and Written Opinion for PCT/US2016/028884, dated Jul. 28, 2016, 16 pages.
International Search Report and Written Opinion for PCT/US2016/064125, dated Mar. 13, 2017, 16 pages.
Related U.S. Appl. No. 15/278,766, "Single-Use Bioreactor Sensor Interface" filed Sep. 28, 2016, 18 pages.
Related U.S. Appl. No. 15/072,128, "Flow Measurement System for Single-Use Containers", filed Mar. 16, 2016, 15 pages.
Second Office Action for Chinese Patent Application No. 201180059710.06, dated Auggust 22, 2014, 12 pages with English translation.
Office Action for Chinese Patent Application No. 201180059710.06, dated Feb. 24, 2014, 12 pages with English translation.
Theory and Practice of pH Measurement, PN 44-6033/rev. D, dated Dec. 2010 by Rosemount Analytical, Emerson Process Management, 40 pages.
First Office Action for Chinese Patent Application No. 201210085580.X, dated Jun. 11, 2014, 14 pages including English translation.
Office Action for Canadian Patent Application No. 2818943, dated Jul. 30, 2014, 2 pages.
First Office Action for Chinese Patent Application No. 201510197804.X, dated Jan. 26, 2017, 21 pages including English translation.
Patent Examination Report No. 1 for Australian Patent Application No. 2015253275, dated Nov. 15, 2016, 4 pages.
International Preliminary Report on Patentability for International Patent Application No. PCT/US2015/028192, dated Nov. 17, 2016, 15 pages.
Communication Pursuant to Rules 161(2) and 162 for European Patent Application No. 15786477.8, dated Dec. 9, 2016, 2 pages.
International Search Report and Written Opinion for International Patent Application No. PCT/US2015/028192, dated Jul. 27, 2015, 18 pages.
International Search Report and Written Opinion from International Patent Application No. PCTR/US2011/065032, dated Apr. 26, 2012, 16 pages.
International Search Report and Written Opinion from International Patent Application No. PCTR/US2011/065033, dated Mar. 19, 2012, 16 pages.
Pharmaceutical Industry Solutions: Reliable Liquid Analysis, Brochure by Rosemount Analytical, Emerson Process Management, dated 2005, 12 pages.
S. Schmitmeir et al. Development and Characterization of a Small-Scale Bioreactor Based on a Bioartificial Hepatic Culture Model for Predictive Pharmacological In Vitro Screenings, Biotechnology and Bioengineering, vol. 95, No. 6, dated Dec. 20, 2006, 10 pages.
Application Data Sheet, Tighter pH Control in Pharmaceutical Applications, Jan. 2008, by Rosemount Analytical, Emerson Process Management, 2 pages.
International Search Report and Written Opinion dated Mar. 30, 2018, for International Patent Application No. PCT/US2017/065254, 15 pages.
First Office Action for Chinese Patent Application No. 201710211756.4 dated Nov. 19, 2019, 18pages.
Extended European Search Report dated Jun. 24, 2020 for European Application No. 17882349.8, 7 pages.
Chinese Office Action dated Jul. 3, 2020 for Chinese Patent Application No. 201710211756.4, 33 pages including English translation.
Japanese Office Action dated Sep. 1, 2020 for Japanese Patent Application No. 2020-503861, 9 pages including English translation.

* cited by examiner

SENSOR INTERFACE FOR SINGLE-USE CONTAINERS

BACKGROUND

Single-use containers, such as bioreactors, are useful for generating and supporting biological reactions for any number of purposes. Biological reactions can be susceptible to changes in temperature and/or pressure. Moreover, as the biological reaction progresses, the reaction itself may change various parameters within the bioreactor, such as the pressure. Accordingly, it may be important to monitor pressure or other variables of the biological reaction.

The life sciences industry is moving from large, capital-intensive facilities made of stainless steel with large clean-in-place (CIP) infrastructure to smaller facilities that use polymeric bags or containers functioning as bioreactors. The bioreactor bag is used once and then discarded. This single-use bioreactor technique significantly reduces the capital cost of the plant. For example, in existing facilities that use stainless steel CIP infrastructure, up to 90% of the cost of operating the facility may be due to the clean-in-place infrastructure, including very high end instrumentation designed to withstand a steam cleaning cycle. By moving to disposable, single-use bioreactor bags, the CIP portion of the capital can be eliminated and the facility can be more flexible and much smaller, which, in turn, allows the production of the smaller batches that are needed for more targeted drug therapies and other smaller-scale applications.

As pharmaceutical manufacturers change over from large stainless-steel process vessels to smaller-volume, pre-sterilized, disposable plastic bag systems, there is a need to measure pressure and/or other variables in these systems to control the growth environment and subsequent processes. Typically, pharmaceutical manufacturers and the life science industry in general, have used pressure sensors that are pre-sterilized and are disposed of after a single-use, which, in turn, has driven the life sciences industry to use inexpensive sensors. Such inexpensive sensors use relatively crude methods for fluid isolation, such as silicone gel. These methods can lead to inaccurate measurements, which are generally unacceptable to the life sciences industry for supporting the various biological reactions.

SUMMARY

A single-use sensor interface for coupling a single-use container to a re-usable sensing instrument is provided. The single-use sensor interface includes a polymeric flange couplable to a wall of the single-use container. The polymeric flange has a sidewall and an interface portion configured to receive a deflectable polymeric diaphragm. A deflectable polymeric diaphragm is coupled to the interface portion of the polymeric flange. An instrument coupling portion is sealingly coupled to the polymeric flange.

Another single-use sensor interface for coupling a single-use container to a re-usable sensing instrument includes a polymeric hose adapter and at least one instrument attachment portion. The polymeric hose adapter portion has at least one hose barb configured to retain a hose slid thereover. The hose adapter portion has at least one interface portion that is configured to receive a deflectable polymeric diaphragm. A deflectable polymeric diaphragm is coupled to the interface portion. At least one instrument attachment portion is coupled to the hose adapter portion. The at least one instrument attachment portion has a cylindrical sidewall configure to receive a remote seal assembly or a measuring instrument.

DETAILED DESCRIPTION OF ILLUSTRATIVE EMBODIMENTS

Embodiments of the present invention generally leverage a polymeric sensor interface that couples a single-use container, such as a bioreactor, to a high-precision, re-usable pressure measuring instrument. Accordingly, the actual sensor that measures the pressure within the bioreaction vessel is disposed within the high-precision pressure measurement instrument. In some embodiments, a remote seal system is formed of a polymeric material that is pre-sterilized and may be physically coupled to a pre-sterilized single-use bioreactor. In other embodiments, the polymeric sensor interface may be coupled directly to a re-usable measuring instrument, such as a pressure transmitter. Accordingly, the bioreactor as well as the polymeric sensor interface are disposable. This allows the use of an accurate and precise re-usable pressure transmitter but still provides the end user with a pre-sterilized connection to the bioreaction vessel. The field instrument-side and the process-side couplings will be described separately below. Embodiments of the present invention include any combination of the various process-side configurations with any of the various instrument-side configurations.

Figure 1:
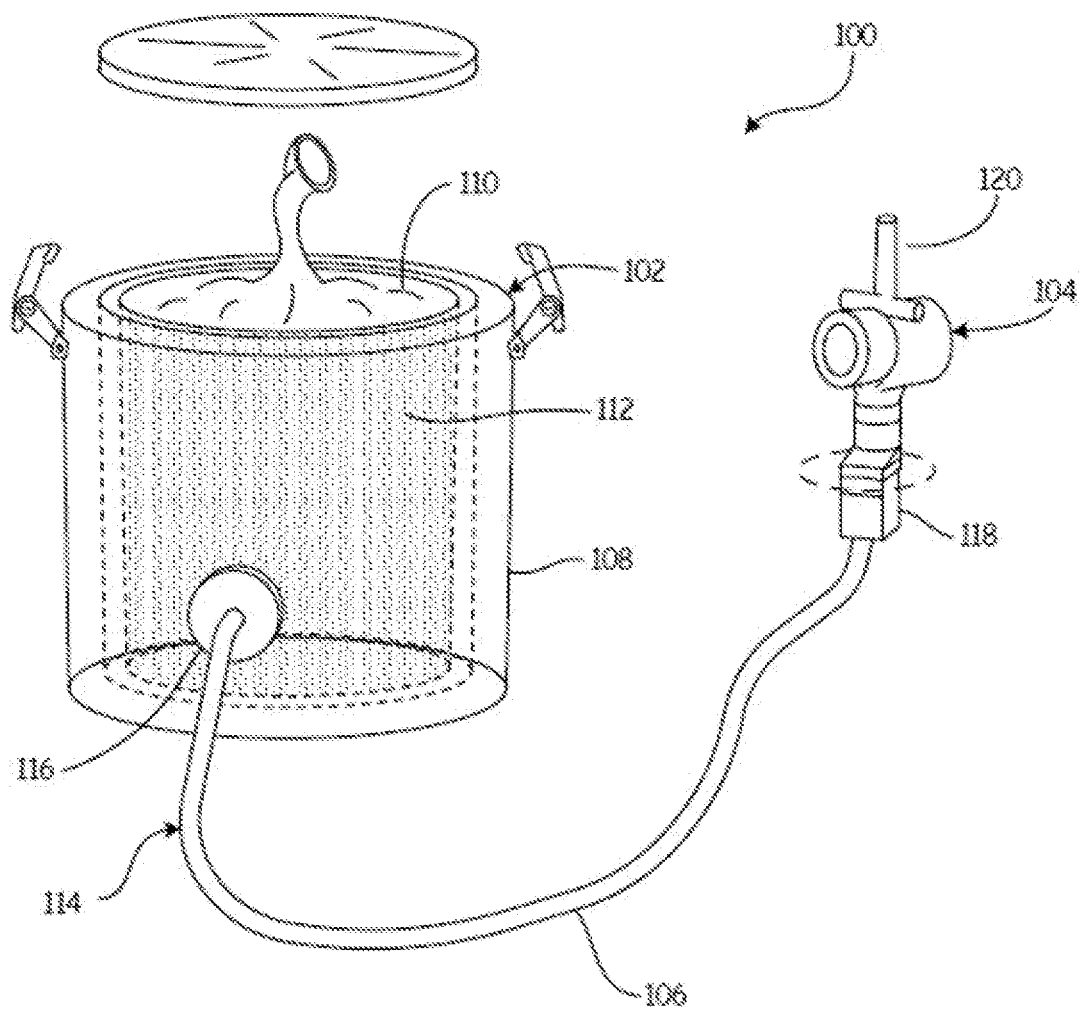
FIG. 1 is a diagrammatic view of single-use bioreactor employing a polymeric sensor interface in accordance with an embodiment of the present invention.

FIG. 1 is a diagrammatic view of a single-use bioreactor employing a polymeric sensor interface in accordance with an embodiment of the present invention. Bioreaction system 100 includes bioreactor 102 coupled to pressure measuring instrument 104 via fluidic coupling 106. Bioreactor 102 generally includes an outer support container 108 that has a wall that is relatively solid such that it forms a shell for single-use bioreaction bag 110 disposed therein. Outer shell 108 is generally matched to the dimensions and functionality of single-use bioreaction bag 110. However outer shell 108 is typically a reusable item. Single-use bioreactor bag 110 is generally a polymeric bag that is configured to support a biological reaction occurring within sample 112.

Polymeric remote seal system 114 couples the pressure within single-use bioreactor bag 110 to pressure measuring instrument 104. This coupling is a fluidic coupling such that pressure acting against a diaphragm disposed proximate process connection 116 generates movement of fluid within coupling 106 to cause associated movement at a diaphragm proximate instrument coupling 118. Such movement conveys the fluid pressure from bioreactor bag 110 to a pressure sensor within instrument 104 such that the pressure can be measured very accurately. Moreover, instrument 104 generally includes characterization and/or calibration information in order to compensate for variations in temperature and/or other environmental variables. Further, various embodiments of instrument 104 may also perform diagnostics relative to the device itself and/or the biological reaction in order to provide additional information instead of simply reporting the pressure within single-use bioreactor bag 110. Further still, instrument 104 may also be configured to convey the pressure information to one or more additional devices via a process communication loop or segment, such as that in accordance with the Highway Addressable Remote Transducer (HART®) protocol or the FOUNDATION™ Fieldbus protocol. Moreover, embodiments described herein may also include wirelessly transmitting such pressure information to any suitable device via antenna 120 in accordance with a wireless process communication protocol, such as IEC62591. In one embodiment, instrument 104 is a commercially-available hygienic pressure transmitter sold under the trade designation Model 3051HT available from Emerson Automation Solutions of Shakopee, Minn.

Embodiments described herein provide a convenient way to measure variables within a single-use container while still ensuring that high quality measurements are used. The polymeric sensor interface can be disposed of or left with the single-use container once the container is empty or replaced. This allows the use and re-use of an accurate, complex wireless measurement instrument with different single-use containers without cleaning as the instrument is isolated from the single-use container. When active monitoring of a single-use container is no longer required, the polymeric interface can be disconnected from the measuring instrument or gauge and disposed or left with the single-use container. Then, the same measuring instrument or gauge can be coupled to another polymeric sensor interface of another single-use container.

Figure 2:
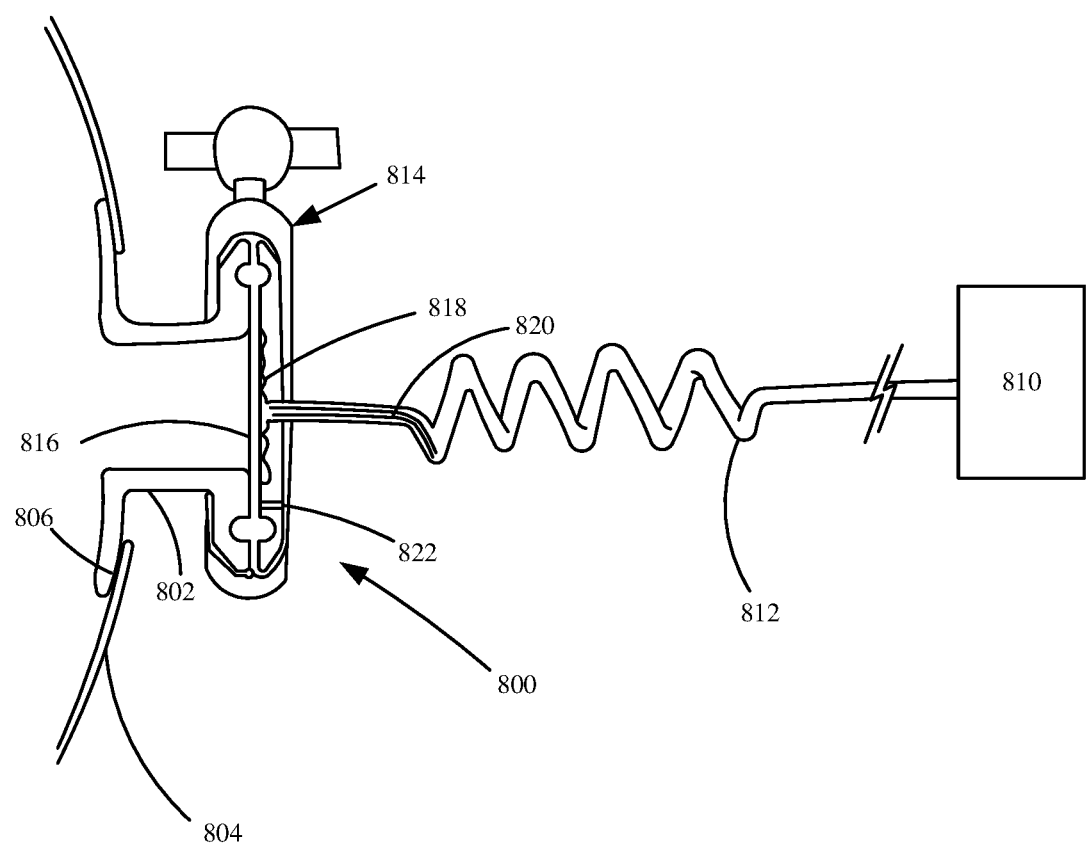
FIG. 2 is a diagrammatic view of a lightweight, flexible pressure transmitter process extension that interfaces with single-use biopharmaceutical bioreactor plastic bag type vessels, in accordance with an embodiment of the present invention.

FIG. 2 is a diagrammatic view of a lightweight, flexible pressure transmitter process extension that allows an interface with a single-use biopharmaceutical bioreactor plastic bag type vessel, in accordance with an embodiment of the present invention. As shown in FIG. 2, a diaphragm remote seal 800 is shown having a flange portion 802 that couples to a wall of single-use bioreactor vessel or bag 804. In the embodiment illustrated in FIG. 2, flange 802 is coupled to an inside surface 806 of the sidewall of bioreactor bag 804. Such coupling can be effected using any suitable techniques such as adhesive, ultrasonic welding, heat fusion welding, or other appropriate techniques. Further, while the embodiment shown in FIG. 2 has flange 802 coupled to the inside of side wall 804, it is expressly contemplated that flange 802 could be suitably coupled to an exterior surface thereof. As shown, adapter 800 fluidically couples a pressure within the single-use bioreactor bag 804 to an external pressure sensing device 810. Such coupling is, in one embodiment, through flexible capillary 812. Interface 814 generally houses a pair of flexible diaphragms. A first diaphragm 816 is generally formed of a flexible polymer that may or may not be attached to the single-use process connection. This polymeric membrane isolates the process fluid from pressure sensing device 810. Additionally, a secondary isolation diaphragm 818 is also provided. Isolation diaphragm 818 isolates a fill fluid 820 disposed within flexible capillary 812 from flexibly polymeric membrane 816. Flexible capillary 812, in one embodiment, is formed of stainless steel and is coiled in order to improve its flexibility. As can be appreciated, when isolation diaphragm 818, which, in some embodiments, may be a stainless steel diaphragm, is brought into proximity with flexible polymeric diaphragm 816, it is possible that some gas could become trapped between the diaphragm seal and the isolating membrane. In accordance with one embodiment, an atmospheric vent 822 is provided that allows such trapped gas to escape. In this way, flexible polymeric membrane 816 can be brought into direct contact with isolating diaphragm 818. Fluid pressure within the single-use bioreactor bag 804 acts against flexible membrane 816 which flexes thereby also moving isolation diaphragm 818 causing a movement of fill fluid 820 within flexible capillary 812 which is conveyed to pressure sensing instrument 810 for measurement. Since pressure measurement device 810 is remote from the single-use bioreactor system, it can be reusable and can be a high precision, complex device, such as a process fluid pressure transmitter that may be reused again and again while single-use bioreactors are used and discarded. The advantage over existing single-use sensors for the biopharmaceutical market is that the sensor and electronics (disposed within pressure sensing device 810) can be re-usable and calibrated with high accuracy, and employ stable, proven technology that is able to be integrated with state of the art control systems. While the embodiment shown in FIG. 2 provides a remote seal system, it is expressly contemplated that the re-usable measuring instrument may be directly coupled to the polymeric sensor interface.

While the embodiment described with respect to FIG. 2 illustrates a single-point pressure measurement, other process pressure measurements, such as differential pressure and/or flow measurements can also be used in the single-use biopharmaceutical manufacturing process as well. Further, some of these concepts would apply to other single-use measurement points including differential pressure flow measurement, filter health pressure measurement in tubing, differential pressure-based level measurements, etc. Providing an improved polymeric/isolating diaphragm interface, in accordance with the embodiment shown in FIG. 2, can provide a more confident use of "disposable" isolating membranes for tough chemical corrosion or abrasive applications with traditional diaphragm seals.

Figure 3:
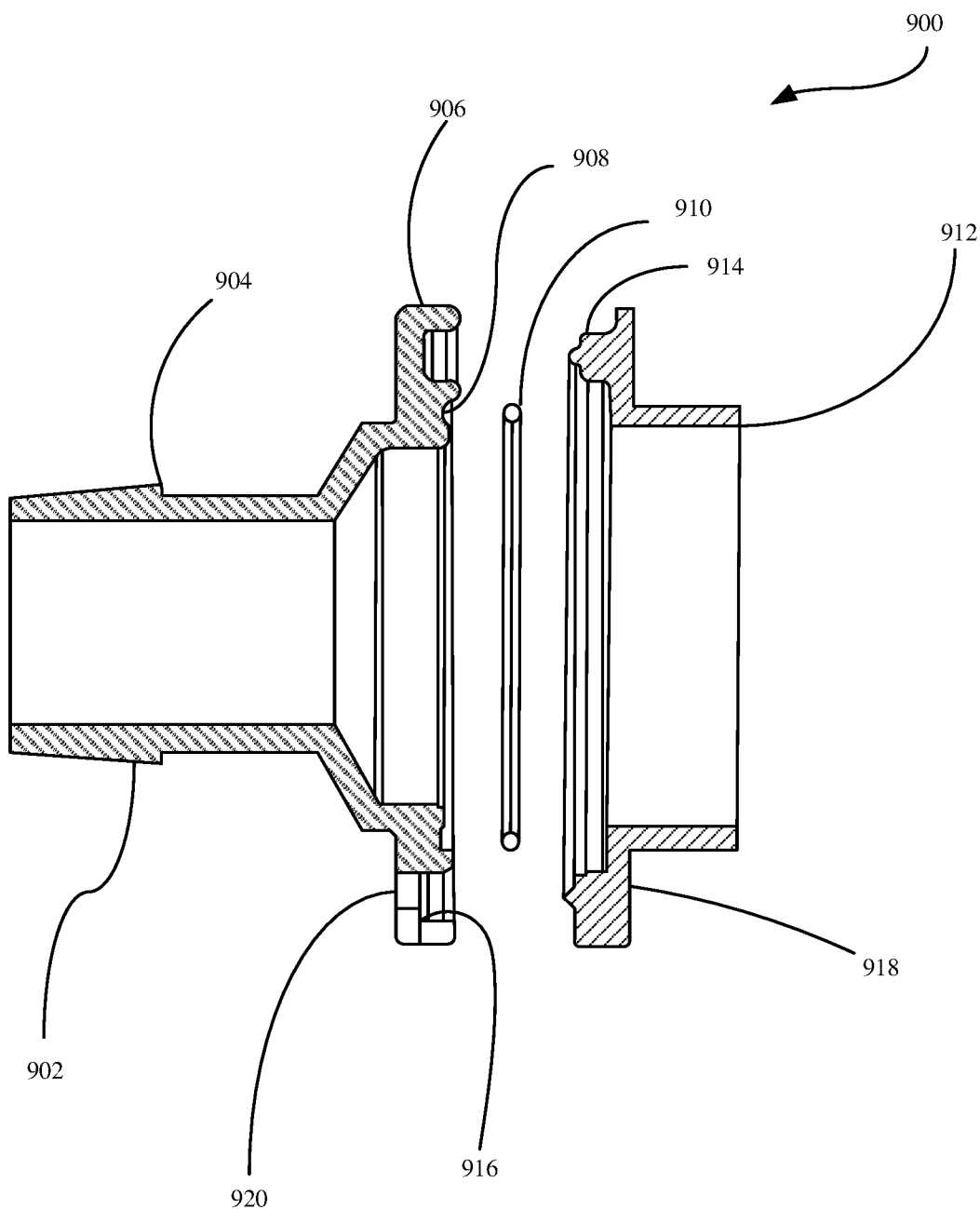
FIG. 3 is a cross-sectional view of an isolating process barrier and adapter that interfaces directly with standard hose barb connections, in accordance with an embodiment of the present invention.

FIG. 3 is a diagrammatic cross-sectional view of a single-use polymeric adapter that can be used with single-use bioreactor bags in accordance with an embodiment of the present invention. It is noted that a number of single-use bioreactor bags employ a tubing barb adapter interface. Such adapters facilitate the coupling of tubing directly to the single-use bioreactor bag. As shown in FIG. 3, adapter 900 includes a hose-adapter portion 902 that, in the illustrated example, includes at least one hose barb 904. Portion 902 is fluidically coupled to interface 906 that includes, in the illustrated example, a groove 908 configured to receive instrument/process barrier 910. While instrument/process barrier 910 is shown having an o-ring profile, embodiments maybe practiced where the profile of barrier 910 is flat and is clamped or otherwise affixed between suitable surface features of portions 902, 912. Examples of such features include ring-shaped ridges or other suitable structures. Instrument attachment portion 912 is configured to mate with hose-adapter portion 902 in order to provide a reusable diaphragm seal that is clamped. In the illustrated embodiment, an annular ring 914 is configured to be received within annular groove 916. Clamping pressure is then applied to surface 918 and 920 in order to urge the assembly together. A re-usable measuring instrument is coupled to the adapter and barrier with, in one embodiment, a bayonet-style locking clamp that provides positive locking feedback and integral damage protection during removal to the diaphragm seal interface that is by nature sensitive to handling damage.

Coupling of the adapter to the re-usable measuring instrument may be through a remote seal arrangement or may be direct coupling. In a remote seal arrangement, instrument attachment portion 912 is still eventually coupled to a pressure measurement instrument such as a process fluid pressure transmitter or other suitable device. Although FIG. 3 is described with respect to clamping portions 902 and 914 together, it is also expressly contemplated that other forms of attaching the portions together can be used, such as ultrasonic welding or plastic welding. Instrument attachment portion 912 may be coupled to a remote seal, such as that shown in FIG. 4, or may be coupled directly to a measurement instrument, such as a pressure transmitter.

Figure 4:
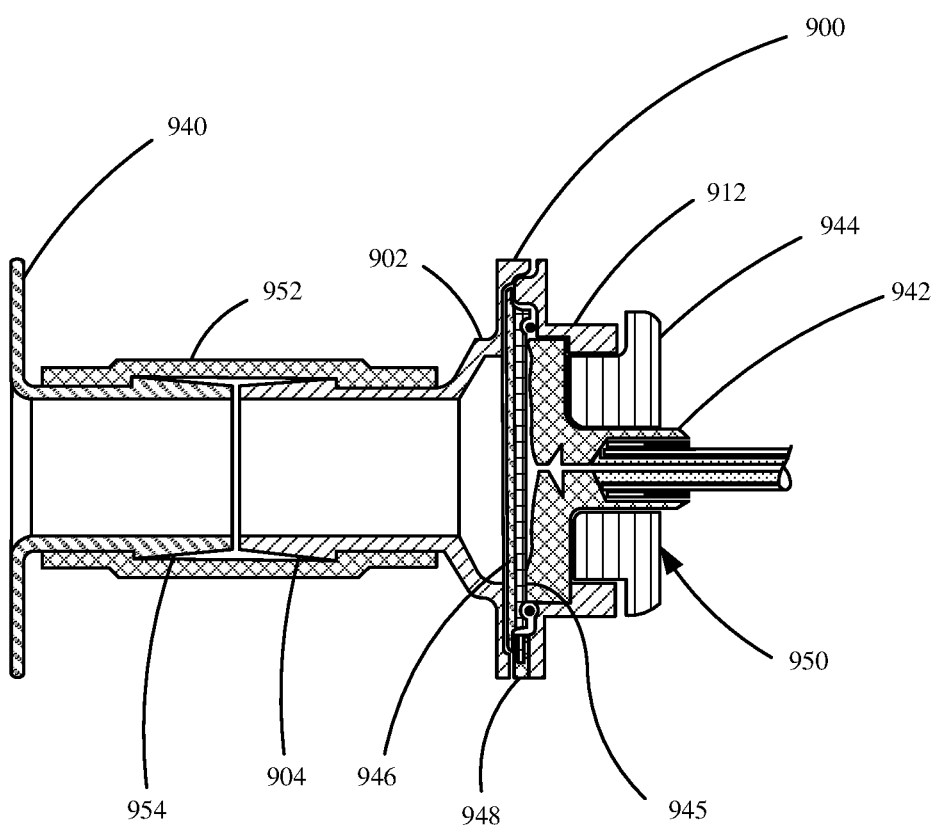
FIG. 4 is a diagrammatic view of the hose barb adapter, in accordance with an embodiment of the present invention, coupled to a hose barb of a single-use bioreactor in accordance with an embodiment of the present invention.

FIG. 4 is a diagrammatic view of adapter 900 coupled to a hose barb port 940 of a single-use bioreactor in accordance with an embodiment of the present invention. In the illustrated embodiment, a remote seal assembly 942 is coupled to instrument portion 912 via a locking clamp 944. As shown, remote seal assembly 942 includes a diaphragm 945 that is, in one embodiment, adjacent flexible polymeric diaphragm 946. In the embodiment shown in FIG. 4, instrument attachment portion 912 and hose barb portion 902 are coupled together using an ultrasonically welded connection 948. However, other forms of coupling can be used. Further, a locking clamp 950 is shown urging remote seal assembly into contact with and sealing against isolation diaphragm 945. However, other forms of clamps and mechanical structures can be used in accordance with embodiments of the present invention. One advantage of the embodiment shown in FIG. 4 is that a standard hose barb bag port 940 can be fluidically interfaced with using simple tubing 952 that extends over the hose barb 954 of hose barb port 940 and hose barb 904 of hose barb portion 902.

Figure 5:
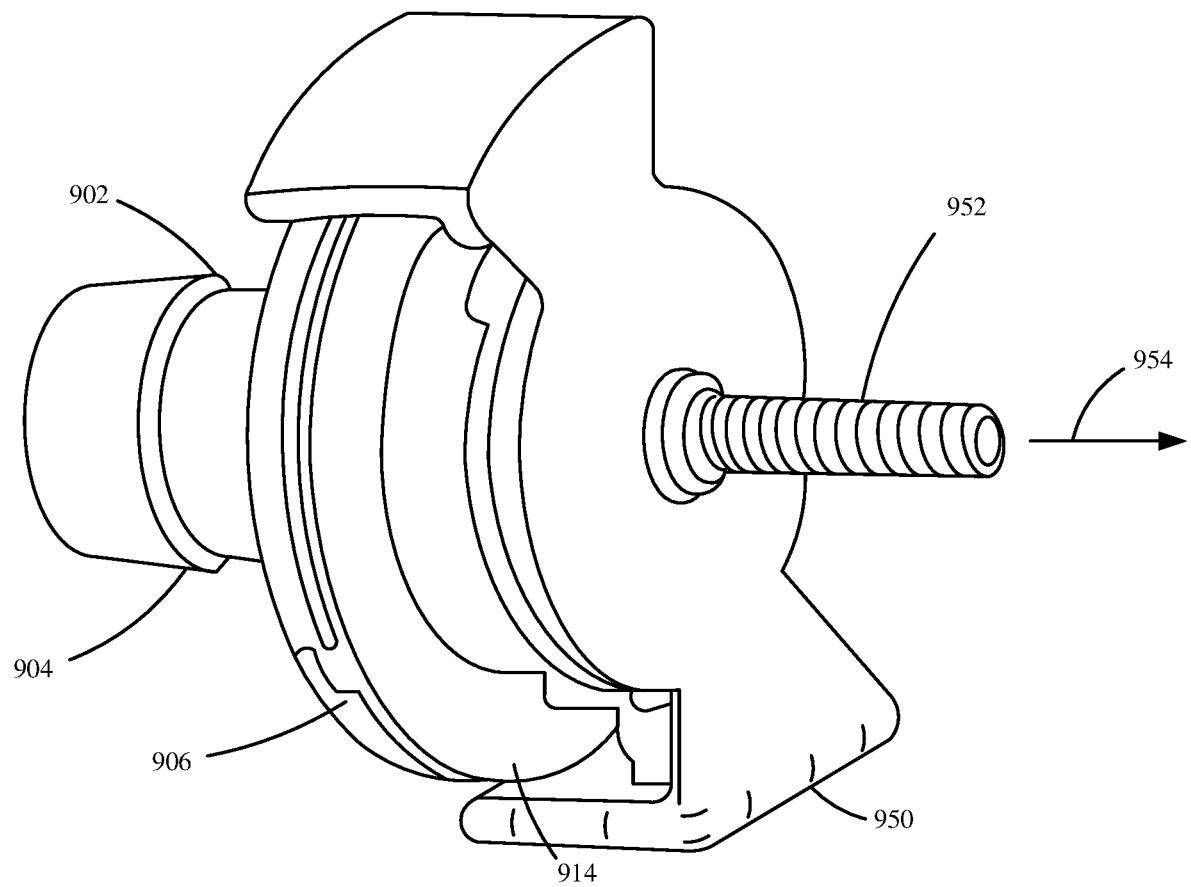
FIG. 5 is a perspective view of an isolating process barrier and adapter in accordance with an embodiment of the present invention.

FIG. 5 is a diagrammatic perspective view of a single-use polymer adapter in accordance with an embodiment of the present invention. FIG. 5 shows the adapter of FIGS. 3 and 4 in perspective. In particular, clamp 950 is better illustrated in FIG. 5 as well as capillary line 952 extending therethrough to a pressure measurement device as indicated by arrow 954.

In accordance with various embodiments of the present invention, a single-use adapter can be provided in various configurations that enable it to be a coupled to a single-use bioreactor bag port; used in line with tubing, for low measurement; or used with standard hose barb bioreactor bag connections (such as the embodiment described with respect to FIGS. 3-5).

Figure 6A:
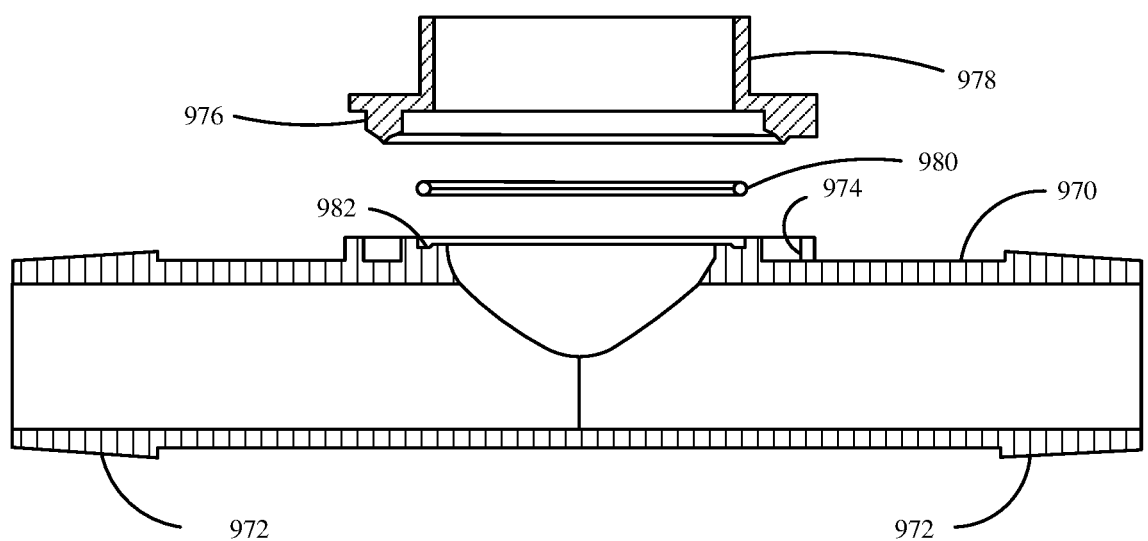
FIGS. 6A and 6B are cross-sectional diagrammatic views of a single-use instrument attachment for coupling to a tee adapter in accordance with an embodiment of the present invention.
Figure 6B:
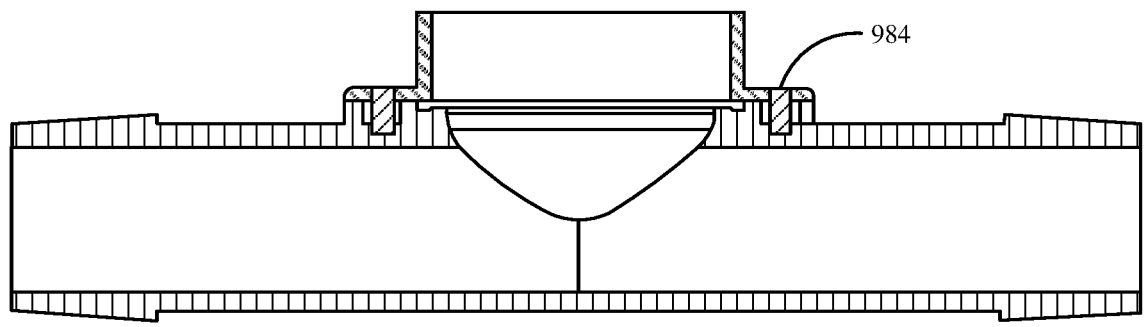

FIG. 6A is a cross-sectional diagrammatic view of a single-use instrument attachment for coupling to a tee adapter in accordance with an embodiment of the present invention. As shown in FIG. 6A, tee adapter 970 includes a pair of hose barbs 972 such that it can be inserted in line with a hose. Additionally, adapter 970 includes a ring-shaped groove 974 that is configured to receive ring 976 of instrument attachment portion 978. A polymeric instrument/process barrier 980 is configured to be received within groove 982 of tee adapter 970. Then, instrument attachment portion 976 is brought into contact with tee 970 such that ring 976 is located within groove 974. Then, as shown in FIG. 6B, a suitable physical attachment, such as a plastic weld 984 is used to join instrument attachment portion 978 to tee 970. Subsequently, a remote seal and clamp, as shown in the embodiment described with respect to FIGS. 3-5, can be used to couple a process measurement instrument, such as a process fluid pressure transmitter to tee 970. Thus, it can be seen that tee 970 is a single-use component that can reliably couple to high precision, complex instrumentation in a way that allows the instrument to be reusable.

Figure 7A:
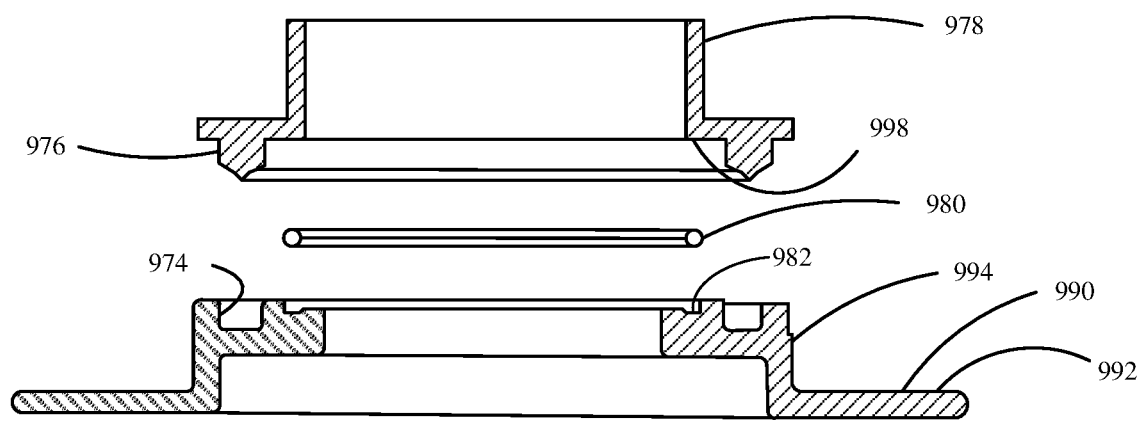
FIGS. 7A and 7B are diagrammatic views of a single-use polymeric adapter in accordance with another embodiment of the present invention.
Figure 7B:
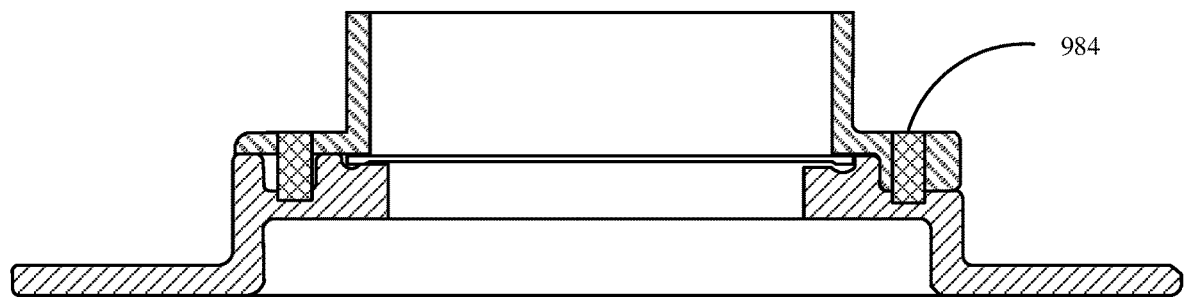

FIG. 7A is a cross-sectional diagrammatic view of a single-use polymeric adapter in accordance with another embodiment of the present invention. The adapter shown in FIG. 7A bears some similarities to the embodiment described with respect to FIG. 6A, and like components are numbered similarly. Bag port adapter 990 is configured to couple to a wall of a single-use bioreactor bag or vessel. Bag port adapter 990 includes a flange 992 that may be coupled to either an inside surface or an outside surface of the bag wall. Such coupling can be performed in any suitable manner, including the use of an adhesive, ultrasonic welding, plastic welding, or other suitable techniques. Bag port adapter 990 includes a raised portion 994 that has a ring-shaped groove 974 that is configured to receive ring 976 of instrument attachment portion 978. Additionally, bag port adapter 990 also includes a process barrier groove 982 that is sized to receive instrument/process barrier 980. When assembled, instrument attachment portion 978 is brought into contact with bag port adapter 990 such that ring 976 is disposed within groove 974 and surface 998 sealingly urges instrument/process barrier 980 into groove 982. Then, instrument attachment portion 978 is affixed to bag port adapter 990. In one embodiment, this is done using an annular plastic weld 984, as shown in FIG. 7B.

Figure 8A:
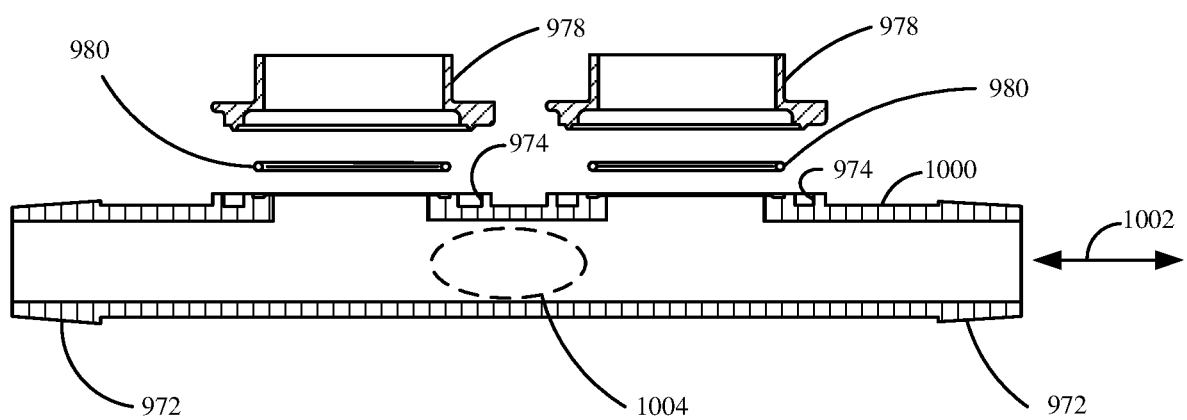
FIGS. 8A and 8B are diagrammatic views of a single-use polymeric adapter in accordance with an embodiment of the present invention.
Figure 8B:
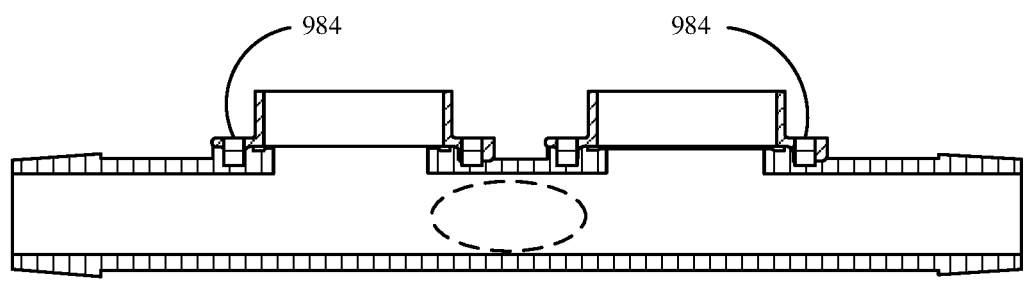

FIGS. 8A and 8B show an embodiment of the present invention where a plurality of instrument attachment portions 978 are coupled to a flow measurement tee 1000 in accordance with an embodiment of the present invention. Various components illustrated with respect to the embodiment of FIGS. 8A and 8B are similar to components described above, and like components are numbered similarly. Tee 1000 includes a pair of instrument attachment portions 978 that are spaced along a flow direction 1002 such that an obstruction placed within intermediate region 1004 will create a pressure difference that is detectable using pressures measured from instrument attachment portions 978. In this way, the addition of a venturi or other suitable restriction to create a differential pressure will allow the embodiment shown in FIG. 8A to measure flow-related values. As can be seen, when the instrument portions 978 are brought into contact with their respective grooves 974, the instrument attachment portions 978 can be attached using any suitable technique including a plastic weld 984 as indicated in FIG. 8B.

Accordingly, various embodiments of the present invention set forth above can employ a single-use polymeric sensor interface or adapter that can be used with single-use bioreactor bags, tubing, or single-use biopharmaceutical manufacturing systems. In some embodiments, a fluid-filled remote diaphragm seal pressure transmitter system can be attached to such an adapter but is separated therefrom by a thin polymeric barrier that is integrated into the adapter. In other embodiments, a measuring instrument, such as a pressure transmitter is coupled directly to the sensor interface. In all such embodiments, the interface seals the contents of the single-use container from the re-usable measuring instrument using a process barrier. This barrier enables the pressure transducer and/or remote diaphragm seal to be reused and also not require sterilization. The single-use adapter has multiple embodiments, as described above, that enable it to be a bag port that is integrated into a single-use bag; used in-line with tubing, for flow measurement or pressure measurement; or used with a standard hose barb bioreactor bag connection.

Embodiments described herein can use a three-piece welded construction of a disposable adapter where the process isolating barrier is captured between the welded process adapter and remote seal connection creating an hermetic barrier while itself remaining un-welded, this allows for more optimal materials to be used for the barrier than other all-welded solutions. Further, some embodiments of the isolating barrier and adapter may interface directly with standard hose barb connections thereby allowing existing off-the-shelf bioreactor bags from multiple vendors to be used without modification or custom weld ports. Finally, reusable diaphragm seals or pressure transducers, in accordance with various embodiments described herein, may be clamped to the adapter and barrier with any suitable type of clamp, such as a bayonet-style locking clamp that may provide positive locking feedback and integral damage protection during removal.

Although the present invention has been described with reference to preferred embodiments, workers skilled in the art will recognize that changes may be made in form and detail without departing from the spirit and scope of the invention.

What is claimed is:

1. A single-use sensor interface for coupling a single-use container to a re-usable sensing instrument, the interface comprising:
    a polymeric flange couplable to a wall of the single-use container, the polymeric flange having a sidewall and an interface portion configured to receive a deflectable polymeric diaphragm;
    a deflectable polymeric diaphragm coupled to the interface portion of the polymeric flange;
    an instrument coupling portion sealingly coupled to the polymeric flange, the instrument coupling portion being configured to couple to the re-usable sensing instrument.

2. The single-use sensor interface of claim 1, wherein the instrument coupling portion is releasably coupled to the polymeric flange using a clamp.

3. The single-use sensor interface of claim 1, wherein the instrument coupling portion includes an isolation diaphragm adjacent to the polymeric diaphragm.

4. The single-use sensor interface of claim 3, wherein the isolation diaphragm is a formed of stainless steel.

5. The single-use sensor interface of claim 1, and further comprising a vent configured to release gas trapped between the deflectable polymeric diaphragm and the isolation diaphragm.

6. The single-use sensor interface of claim 1, wherein the instrument coup ng portion is plastic welded to the polymeric flange.

7. A single-use sensor interface for coupling a single-use container to a re-usable sensing instrument, the interface comprising:
    a polymeric hose adapter portion having at least one hose barb configured to retain a hose slid thereover, the hose adapter portion having a first surface;
    an instrument coupling portion having a second surface;
    a deflectable polymeric diaphragm press fit between the first and second surfaces; and
    at least one instrument attachment portion coupled to the hose adapter portion, the at least one instrument attachment portion having a cylindrical sidewall.

8. The single-use sensor interface of claim 7, wherein at least one instrument attachment portion is plastic welded to the hose adapter portion.

9. The single-use sensor interface of claim 7, wherein the at least one instrument attachment portion is ultrasonically welded to the hose adapter portion.

10. The single-use sensor interface of claim 7, wherein the polymeric hose adapter portion includes an input and an output fluidically coupled together and wherein the at least one hose barb includes a first hose barb disposed proximate the input and a second hose barb disposed proximate the output.

11. The single-use sensor interface of claim 10, wherein the at least one instrument attachment portion comprises a first instrument attachment portion and a second instrument attachment portion separated from each other along a flow axis.

12. The single-use sensor interface of claim 11, and further comprising a flow restriction disposed within the hose adapter portion between the first instrument attachment portion and the second instrument attachment portion.

13. The single-use sensor interface of claim 7, wherein the polymeric hose adapter portion is disposed adjacent a hose barb bag port of the single-use container and wherein a length of tubing is disposed over the hose barb bag port and at least one hose barb of the hose adapter portion.

* * * * *

UNITED STATES PATENT AND TRADEMARK OFFICE
CERTIFICATE OF CORRECTION

PATENT NO. : 10,836,990 B2
APPLICATION NO. : 15/390154
DATED : November 17, 2020
INVENTOR(S) : Paul R. Fadell et al.

Page 1 of 1

It is certified that error appears in the above-identified patent and that said Letters Patent is hereby corrected as shown below:

On the Title Page

Item (73), Assignee should read: Rosemount Inc., Shakopee, MN (US)

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*